United States Patent [19]

Plummer

[11] Patent Number: 5,334,363

[45] Date of Patent: * Aug. 2, 1994

[54] PROCESS FOR RECOVERING SULFUR AND HYDROGEN FROM HYDROGEN SULFIDE

[75] Inventor: Mark A. Plummer, Littleton, Colo.

[73] Assignee: Marathon Oil Company, Findlay, Ohio

[*] Notice: The portion of the term of this patent subsequent to Jan. 10, 2010 has been disclaimed.

[21] Appl. No.: 983,936

[22] Filed: Dec. 1, 1992

[51] Int. Cl.$^5$ ............................................. C01B 17/16
[52] U.S. Cl. ............................... 423/226; 423/243.01; 423/576.4
[58] Field of Search .................. 423/220, 226, 576.4, 423/651, 243.01

[56] References Cited

U.S. PATENT DOCUMENTS

| | | | |
|---|---|---|---|
| 2,994,589 | 8/1961 | Stolfa et al. | 23/293 S |
| 3,984,425 | 10/1976 | Mori et al. | 260/378 |
| 4,100,256 | 7/1978 | Bozzelli et al. | 423/220 |
| 4,176,125 | 11/1979 | Matsuura et al. | 260/369 |
| 4,592,905 | 6/1986 | Plummer et al. | 423/573 R |
| 4,847,429 | 7/1989 | Lentz et al. | 268/643 |
| 5,180,572 | 1/1993 | Plummer | 423/576.7 |

FOREIGN PATENT DOCUMENTS 50-145367 11/1975 Japan .................................... 423/226

OTHER PUBLICATIONS

M. A. Plummer, Sulfur and Hydrogen from H2, Hydrocarbon Processing, Apr. 1987, pp. 38-40.

*Primary Examiner*—Gary P. Straub
*Assistant Examiner*—Timothy C. Vanoy

[57] ABSTRACT

A process for converting hydrogen sulfide which is contained in a gaseous feed stream to elemental sulfur and hydrogen. The process comprises contacting said gaseous feed stream with a polar organic solvent having an anthraquinone, and optionally a complexing agent, dissolved therein, reacting the hydrogen sulfide gas and anthraquinone to produce sulfur and an anthrahydroquinone in the solvent, and catalytically dehydrogenating the anthrahyroquinone to anthraquinone and hydrogen. In accordance with the present invention, a relatively small quantity of water is added to a polar organic solvent thereby increasing the elemental sulfur which is precipitated and thus recovered. The addition of water prior to or during sulfur production also increases hydrogen product selectivity in the subsequent dehydrogenation of anthrahydroquinone.

31 Claims, 4 Drawing Sheets

PROCESS FOR RECOVERING SULFUR AND HYDROGEN FROM HYDROGEN SULFIDE

BACKGROUND OF THE INVENTION

1. Field of the Invention

The present invention relates to a process for converting hydrogen sulfide which is contained in a gaseous feed stream to elemental sulfur and hydrogen by initially reacting hydrogen sulfide with an anthraquinone which is dissolved in a polar organic solvent wherein a relatively small quantity of water is added to the polar organic solvent thereby increasing the elemental sulfur which is recovered, and more particularly, to such a process wherein the relatively small quantity of water which is added to the solvent during the initial reaction stage also increases hydrogen product selectivity in the subsequent dehydrogenation of anthrahydroquinone which is formed in the initial reaction.

2. Description of Related Art

Many processes relating to the petroleum industry generate gaseous by-products containing hydrogen sulfide, either alone or in a mixture with other gases, for example, methane, carbon dioxide, nitrogen, etc. For many years, these gaseous by-products were oxidized by common oxidation processes, such as, the Claus process, to obtain sulfur. In accordance with the Claus process, hydrogen sulfide is oxidized by direct contact with air to produce sulfur and water. However, several disadvantages of air oxidation of hydrogen sulfide, including loss of a valuable hydrogen source, precise air rate control, removal of trace sulfur compounds from spent air, and an upper limit on the ratio of carbon dioxide to hydrogen sulfide, led to the development of alternative processes for the conversion of hydrogen sulfide in gaseous by-products to sulfur.

As detailed in U.S. Pat. No. 4,592,905 to Plummer et al., one such alternative process involves contacting within a reactor a feed gas containing hydrogen sulfide with an anthraquinone which is dissolved in a polar organic solvent. This polar organic solvent preferably has a polarity greater than about 3 Debye units. The resulting reaction between hydrogen sulfide and anthraquinone yields sulfur and the corresponding anthrahydroquinone. The sulfur formed from the reaction between hydrogen sulfide and anthraquinone precipitates from the solution in crystalline form ($S_8$) and is recovered as a product. However, the polymerization and precipitation of the sulfur formed as $S_8$ has remained a limiting factor in this process. The amount of sulfur recoverable as an $S_8$ product has been an unacceptable percentage of the total sulfur formed and the time required to precipitate $S_8$ as a product is sufficiently long to impede the commercial viability of the process.

The remaining solution containing anthrahydroquinone is thermally or catalytically regenerated thereby producing the initial anthraquinone form and releasing hydrogen gas. The anthraquinone is recycled back to the reactor and the hydrogen gas is recovered as a product. Regeneration or dehydrogenation of anthrahydroquinone using metal supported catalysts causes hydrogenolysis which results in the undesirable production of water and anthrones and/or anthranols. Thus, a need exists for such a process wherein the amount of sulfur which can be precipitated from solution in crystalline form ($S_8$) and recovered as a product is increased. A further need exists to increase the selectivity of anthrahydroquinone to anthraquinone and hydrogen product in such a process, and thus, decrease unwanted hydrogenolysis by-products, such as anthrones and/or anthranols.

Accordingly, it is an object of the present invention to provide a process for increasing the amount of sulfur obtained from the reaction between hydrogen sulfide and anthraquinone which can be precipitated from solution in crystalline form ($S_8$) and recovered as a product.

It is a further object of the present invention to provide a process for increasing hydrogen production selectivity during dehydrogenation of anthrahydroquinone, and thus, decrease unwanted hydrogenolysis by-products.

It is a still further object of the present invention to provide a process wherein sulfur which is formed by the reaction between hydrogen sulfide and anthraquinone can be precipitated from solution in crystalline form ($S_8$) in a commercially acceptable time.

SUMMARY OF THE INVENTION

To achieve the foregoing and other objects, and in accordance with the purposes of the present invention, as embodied and broadly described herein, one characterization of the present invention is a process for converting hydrogen sulfide gas to sulfur. The process comprises contacting a feed gas which contains the hydrogen sulfide gas with a polar organic solvent having an anthraquinone anti water dissolved therein and reacting the hydrogen sulfide gas with the anthraquinone to produce sulfur and an anthrahydroquinone in the solvent. In accordance with this embodiment of the present invention, water is dissolved in the solvent in an amount of from about 0.5 to about 5.0 moles of the water to moles of the anthraquinone so as to increase the amount of sulfur produced.

In another characterization of the present invention, the process of for converting hydrogen sulfide gas to sulfur comprising contacting the hydrogen sulfide gas with a polar organic solvent having an anthraquinone and water dissolved therein, reacting the hydrogen sulfide gas with the anthraquinone to produce sulfur and an anthrahydroquinone, and dehydrogenating the anthrahyroquinone to anthraquinone and hydrogen. The water is dissolved in the solvent in an amount of from about 0.5 to about 5.0 moles of water to moles of anthraquinone so as to increase the selectivity of anthrahydroquinone conversion to anthraquinone and hydrogen by inhibiting hydrogenolysis.

BRIEF DESCRIPTION OF THE DRAWINGS

The accompanying drawings, which are incorporated in and form a part of the specification, illustrate the embodiments of the present invention and, together with the description, serve to explain the principles of the invention.

In the drawings.

DETAILED DESCRIPTION OF THE PREFERRED EMBODIMENTS

Figure 1:
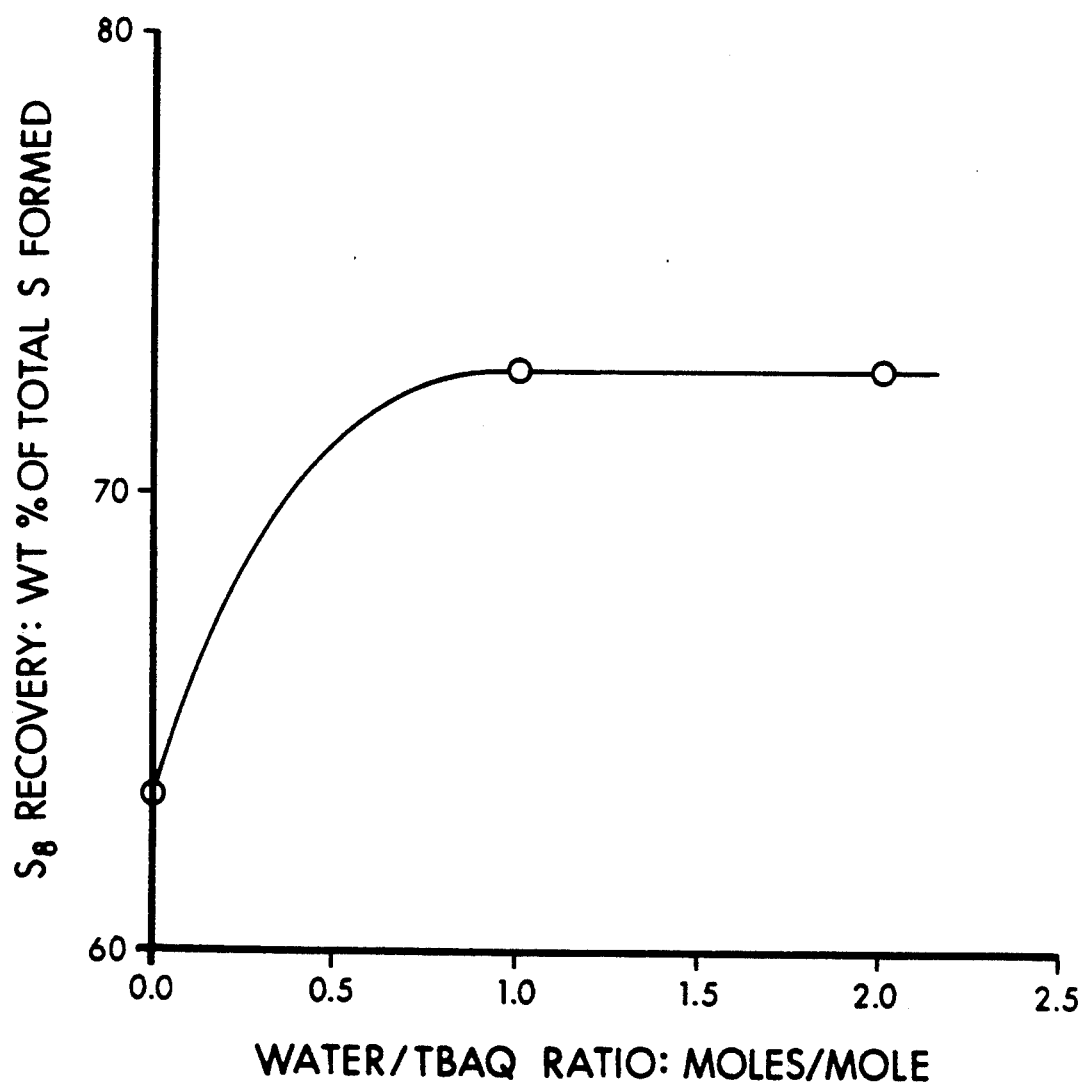
FIG. 1 is a graph which depicts sulfur ($S_8$) recovery as a function of the molar ratio of water to t-butyl anthraquinone (TBAQ) in the process of the present invention.

The present invention relates to a process wherein a feed gas containing hydrogen sulfide ($H_2S$) and an anthraquinone, dissolved in a polar organic solvent, are contacted in a reactor. The polar organic solvent may also contain a complexing agent, both of which are selected in accordance with commonly assigned, copending application entitled "Hydrogen Sulfide Conversion Process" which was filed on Dec. 1, 1992 and assigned a Ser. No. of 07/984,140. The complexing agent reacts with hydrogen sulfide to form an ion complex. Should the feed gas contain large quantities of gases other than hydrogen sulfide which are inert to the process, such as nitrogen, methane or other low molecular weight hydrocarbons, the feed gas and polar organic solvent containing an anthraquinone and a complexing agent may be initially contacted in an absorber. The feed gas may contain other sulfur compounds, such as COS, $CS_2$ and mercaptans, which are converted in the process to $H_2S$, recycled, and converted to sulfur. The solvent preferentially solubilizes hydrogen sulfide from the feed gas to form a reaction solution which is maintained in the reactor at a temperature of from about 0° C. to about 70° C. and an $H_2S$ partial pressure of from about 0.05 to about 4.0 atmospheres and for a time which is sufficient to convert the hydrogen sulfide and anthraquinone to sulfur and anthrahydroquinone.

The insoluble sulfur, e.g. $S_8$ or other forms of polymerized sulfur, is withdrawn from the reactor as a precipitate in the reaction solution, is separated from solution by filtration, centrifugation or other means known in the art, is washed to remove the polar organic solvent and dissolved anthrahydroquinone, any unreacted anthraquinone and complexing agent, and is dried or melted to a liquid form.

Suitable polar organic solvents include N-methyl-2-pyrrolidinone, N,N-dimethylacetamide, N,N-dimethylformamaide, sulfolane (tetrahydrothiophene-1,1-dioxide), acetonitrile, 2-nitropropane, propylene carbonate and mixtures thereof. The most preferred solvent is N-methyl-2-pyrrolidinone (NMP). Useful anthraquinones are ethyl, t-butyl, t-amyl and s-amyl anthraquinones and mixtures thereof because of their relatively high solubilities in most polar organic solvents. The $pK_b$ of the complexing agent utilized, if any, is less than about 13.0, more preferably less than about 9.0, and most preferably less than about 6.0. The $pK_b$ values are based on $K_w$ (equilibrium constant) of 14.0 for the dissociation of water. Suitable complexing agents are selected from amines, amides, ureas, nitrogen containing heterocyclic aromatics, quanidines, imidazoles, and mixtures thereof. These complexing agents can also be substituted with alkyl, aryl and organic alcohol groups. Examples of suitable complexing agents are n-methylacetamide, pyridine, substituted pyridines, diethylmethylamine, methyldiethanolamine and tetramethylurea. The preferred complexing agents are diethylmethylamine (DEMA), methyldiethanolamine (MDEA), pyridine (PY), and substituted pyridines. The molar ratio of complexing agent to anthraquinone in the polar organic solvent is about 1:32 to about 1:1, preferably about 1:16 to about 1:2, and most preferably about 1:5.

In accordance with the present invention, a small quantity of water is added and dissolved into the reaction solution prior to or in the $H_2S$ reactor. As utilized throughout this specification, the term "water" encompasses fresh water, tap water, deionized water, water free of acidic components, etc. The amount of water added to the reaction solution is from about 0.5 to about 5.0 moles of water to moles of anthraquinone, more preferably from about 0.75 to about 2.0, and most preferably from about 1.0 to about 1.5. The addition of water to the reaction solution results in an unexpected increase in the recovery of sulfur formed during the conversion of hydrogen sulfide and anthraquinone to sulfur and anthrahydroquinone. While it is not exactly understood why the addition of water to the reaction solution increases the amount of sulfur which can be recovered from the reaction solution, it is believed that the addition of a small amount of water to the reaction solution likely limits the total solution solubility and water is selectively solubilized over sulfur, i.e. $S_8$.

As discussed above, the reaction solution is removed from the $H_2S$ reactor and sulfur is separated therefrom by filtration, centrifugation, or any other means known in the art. This remaining reaction solution is then heated to from about 100° C. to about 150° C. at atmospheric pressure and fed to a flash tank where substantially all unreacted feed gas constituents, including $H_2S$, $CO_2$, and complexing agent, if desired, are removed from solution and recycled to the reactor. The solution is withdrawn from the flash tank and may be further heated to from about 150° C. to about 350° C. at a pressure sufficient to prevent solvent boiling. The heated solution is then fed to a dehydrogenation reactor where the anthrahydroquinone is catalytically or thermally converted to anthraquinone and hydrogen gas ($H_2$) under the temperature and pressure conditions stated above. In accordance with the present invention, Applicant has discovered that the presence of a small amount of water dissolved in the heated solution fed to the dehydrogenation reactor unexpectedly increases hydrogen production selectivity during dehydrogenation of anthrahydroquinone, and thus, decreases unwanted hydrogenolysis by-products, such as anthrones and/or anthranols. Further, increased hydrogen product selectivity occurs in accordance with the present invention at dehydrogenation temperatures, e.g. 150° to 250° C., which previously yielded lower conversion rates. After the dehydrogenation reaction, anthraquinone in its initial form is withdrawn from the dehydrogenation reactor dissolved with the complexing agent in the polar organic solvent and is recycled to the $H_2S$ reactor, while the $H_2$ gas is recovered as a commercial product. Preferably, the process of the present invention is operated as a continuous process, While it is not expressly understood why the addition of water to the polar organic solvent prior to or in the sulfur production stage of the process of the present invention results in increased hydrogen product selectivity in the dehydrogenation stage of the process, it is believed that water addition in the sulfur production stage substantially eliminates the production of the free radicals at this stage which are necessary for anthranol production in the later dehydrogenation stage. Anthrone production is effectively eliminated by operating at temperatures less than about 265° C.

The following examples demonstrate the practice and utility of the present invention, but are not to be construed as limiting the scope thereof.

EXAMPLE 1

Figure 2:
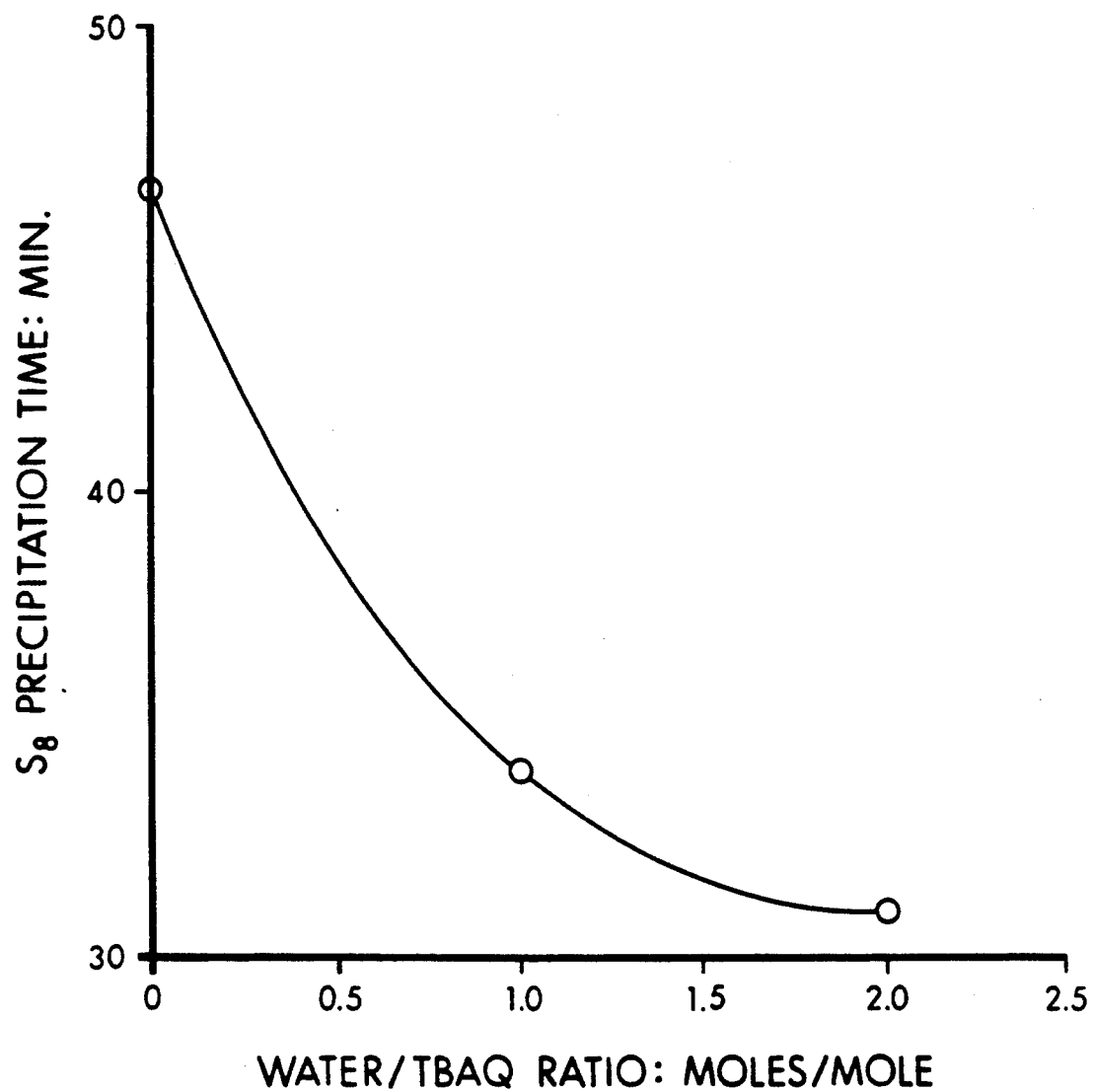
FIG. 2 is a graph which depicts the time for sulfur ($S_8$) precipitation as a function of the molar ratio of water to t-butyl anthraquinone (TBAQ) in the process of the present invention.
Figure 3:
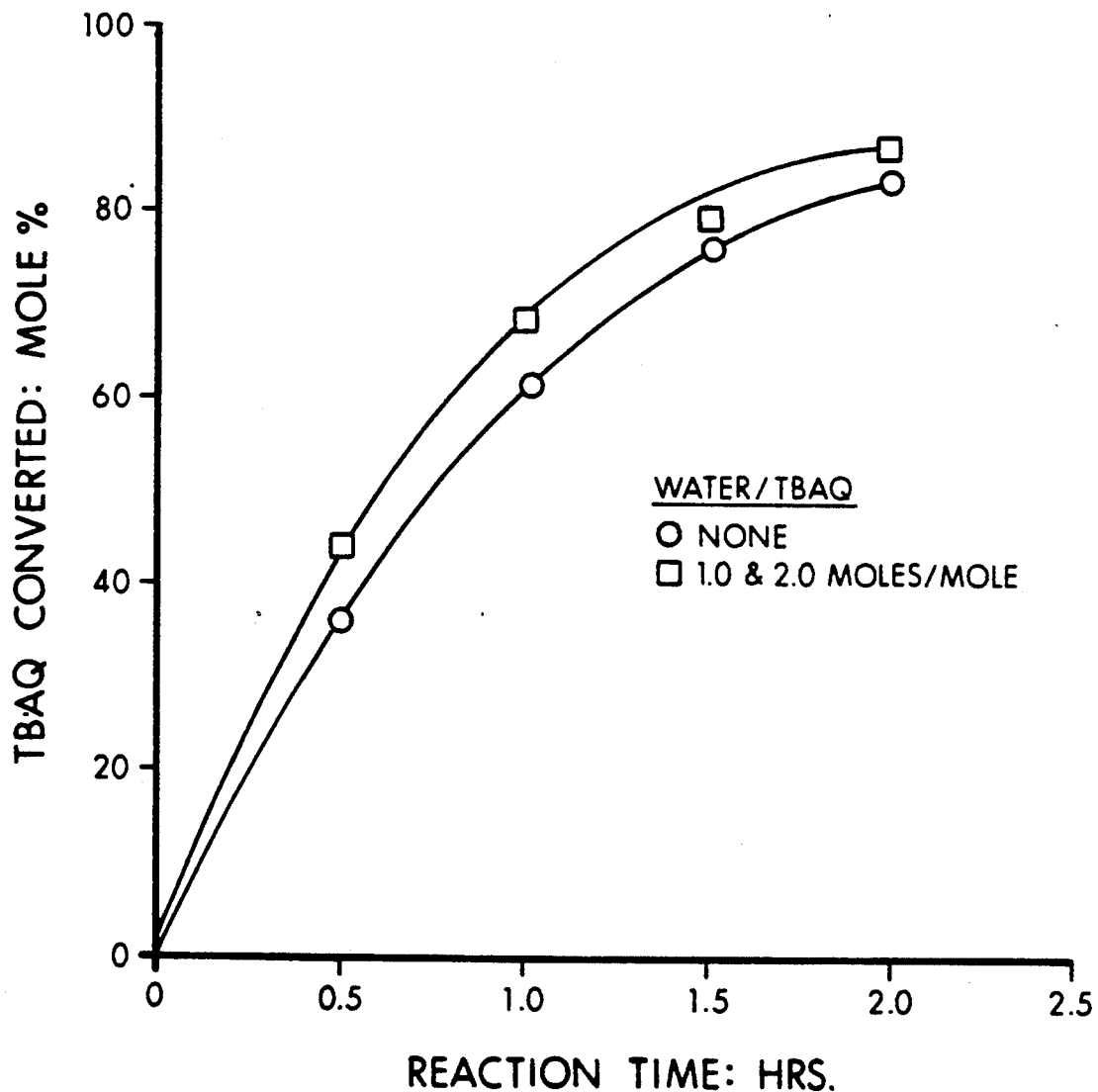
FIG. 3 is a graph which depicts the weight percent of t-butyl anthraquinone (TBAQ) as a function of the reaction time for feeds having varying molar ratios of water to t-butyl anthraquinone (TBAQ) in the process of the present invention.

T-butyl anthraquinone (TBAQ) is added to N-methyl-2-pyrrolidinone (NMP) in an amount of 25 wt %. Pyridine (PY) is also added to the solution as a complexing agent in a molar ratio of complexing agent to TBAQ of 1/1. Varying amounts of water are added to separate portions of the solution. Each portion of the solution is contacted with hydrogen sulfide containing gas in a suitable reactor at a temperature of 20° C. and at a $H_2S$ partial pressure of 1.5 atmospheres for 2 hours. The amount of $S_8$ recovered is determined by weighing the sulfur which is precipitated out of the solution removed from the reactor. The results are graphically illustrated in FIGS. 1-3. As illustrated in FIG. 1, the amount of $S_8$ recovered, which is expressed as the weight % of total sulfur formed in the reactor, increases with increasing amounts of water which are added to the solution prior to or during the sulfur production stage of the process, i.e. during the conversion of hydrogen sulfide and anthraquinone to sulfur and anthrahydroquinone. As illustrated in FIG. 2, the time required for $S_8$ precipitation decreases to commercially acceptable levels with increasing water/TBAQ ratios. As further illustrated in FIG. 3, the TBAQ conversion rate to $H_2TBAQ$ increases with increasing water/TBAQ ratios.

EXAMPLE 2

T-amyl anthraquinone (TAAQ) is added to N-methyl-2-pyrrolidinone (NMP) in an amount of 39 wt %. Diethylmethylamine (DEMA) is also added to the solution as a complexing agent in a molar ratio of complexing agent to TAAQ of $\frac{1}{4}$. One such solution does not contain any water, while another solution contains one mole of water per mole of TAAQ. Each of these solutions is contacted with hydrogen sulfide containing gas in separate reactors at a temperature of 20° C. and at a $H_2S$ partial pressure of 1.5 atmospheres for 15 minutes. The amount of $S_8$ recovered is determined by weighing the sulfur which is precipitated out of the solution removed from the reactor. The amount of $S_8$ recovered which is expressed as the weight % of total sulfur formed in the reactor increases from 61% to 78% while the $S_8$ precipitation time decreases from 10 minutes to 7 minutes when water is added to the solution, as opposed to a solution without water.

EXAMPLE 3

Figure 4:
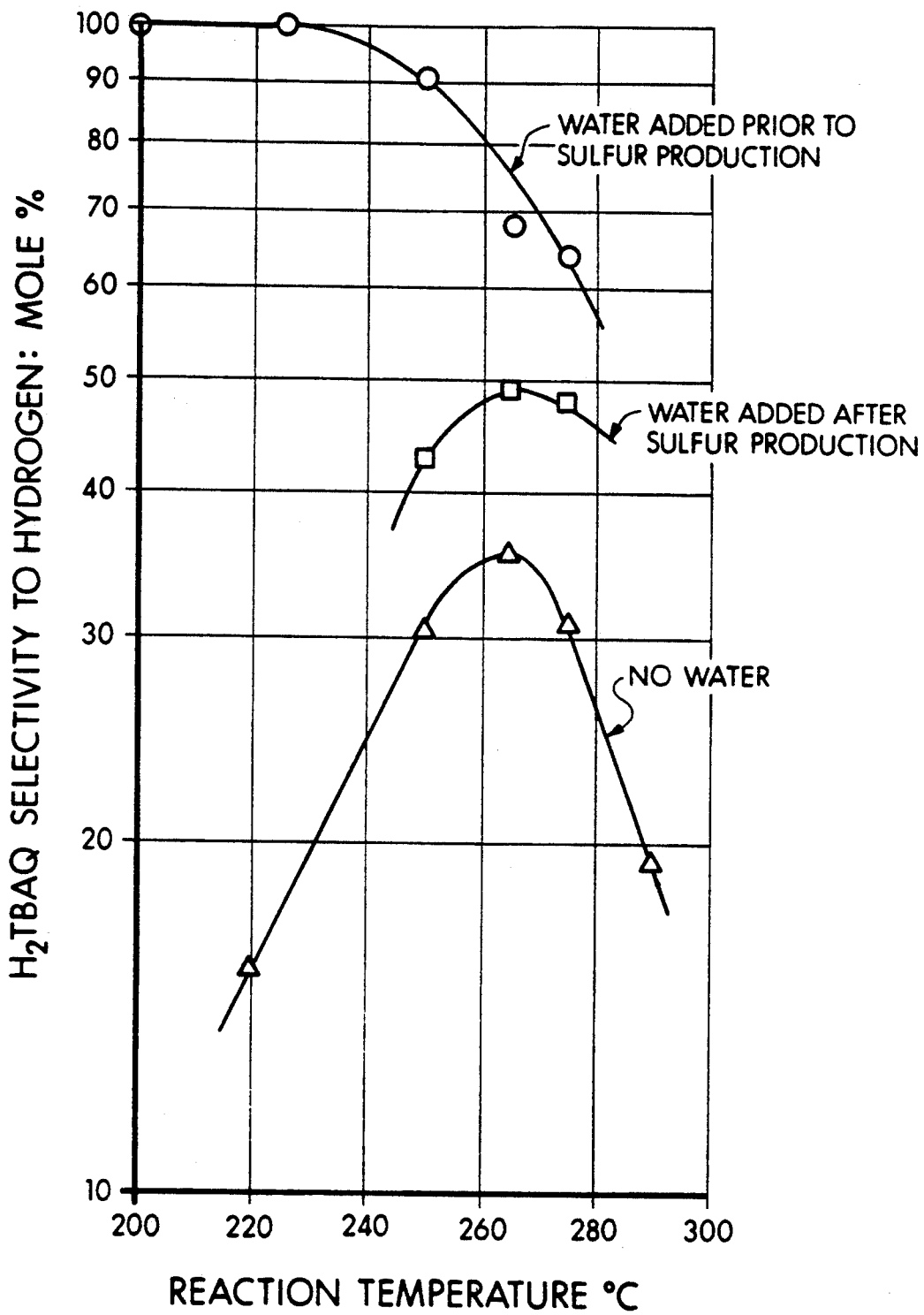
FIG. 4 is a semi-logarithmic graph which depicts the hydrogen production selectivity as a function of the dehydrogenation temperature for separate reaction solutions containing no water, one mole of water per mole of t-butyl anthrahydroquinone ($H_2TBAQ$) added after sulfur production, and one to one and a half moles of water per mole of t-butyl anthraquinone (TBAQ) added prior to the sulfur production stage of the process of the present invention.

A dehydrogenation feed of N-methyl-2-pyrrolidinone (NMP) containing 25 wt % t-butyl anthrahydroquinone ($H_2TBAQ$) is introduced to a reactor wherein the t-butyl anthrahydroquinone is dehydrogenated to t-butyl anthraquinone (TBAQ) and hydrogen in the presence of a platinum catalyst. Dehydrogenation is carried out in the reactor at varying hydrogen pressures of about 2.31 to about 6.12 atmospheres to prevent solution boiling at the varying dehydrogenation temperatures of from about 220° C. to about 290° C. Three separate feeds are reacted under these parameters. Water is not added to one feed, is added to another feed after sulfur production in the amount of 1 mole of water per mole of $H_2TBAQ$, and is added to still another feed prior to sulfur production in an amount of from about 1 to about 1.5 moles of water per mole of TBAQ. Pyridine (PY) is added as a complexing agent to the latter feed in the amount of one mole of pyridine per mole of TBAQ. Each feed is reacted for approximately 1 minute. The results which are illustrated graphically in FIG. 4 indicate that $H_2TBAQ$ selectivity to hydrogen and TBAQ can be increased to 100% below 225° C. if water is added to the NMP solvent prior to the sulfur production stage of the process. Thus, unwanted hydrogenolysis by-products, such as anthrones and/or anthranols, can be effectively eliminated. These results also indicate that the addition of water to the feed after the sulfur production stage of the process described herein, or in the hydrogen production step, improves hydrogen selectivity over the absence of water in the feed. However, in this case, hydrogen selectivity is significantly below the 100% which can be obtained by adding water earlier in the process, i.e. prior to or during the sulfur production stage. Also, hydrogen selectivity decreases both above and below an optimum temperature of about 265° C. when water is added to the feed after the sulfur production stage or in the hydrogen production stage.

From the foregoing, it can be appreciated that the addition of water to the solvent prior to or during the sulfur production stage of the process described herein permits the hydrogen production stage of this process to be operated at temperatures below 265° C. while unexpectedly increasing selectivity to the hydrogen product to about 100%. This reduced temperature requirement translates to reduced reactor design and operating costs.

While the foregoing preferred embodiments of the invention have been described and shown, it is understood that the alternatives and modifications, such as those suggested and others, may be made thereto and fall within the scope of the invention.

I claim:

1. A process for converting hydrogen sulfide to sulfur comprising:
   providing a polar organic solvent having an anthraquinone and water dissolved therein, said water being dissolved in said solvent in an amount of from about 0.5 to about 50 moles of said water to moles of said anthraquinone;
   contacting a feed gas containing hydrogen sulfide with said polar organic solvent; and
   reacting said hydrogen sulfide gas with said anthraquinone to produce sulfur and an anthrahydroquinone in said solvent, said water increasing the amount of said sulfur which is precipitated and recovered from said solvent.

2. The process of claim 1 wherein said amount of water which is added to said solvent is from about 0.75 to about 2.0 moles of said water to moles of said anthraquinone.

3. The process of claim 2 wherein said amount of water which is added to said solvent is from about 1.0 to about 1.5 moles of said water to moles of said anthraquinone.

4. The process of claim 1 wherein said solvent has a complexing agent dissolved therein, said complexing agent reacting with said hydrogen sulfide to form an ion complex.

5. The process of claim 4 wherein said complexing agent is amines, amides, ureas, nitrogen containing heterocyclic aromatics, quanidines, imidazoles, or mixtures thereof.

6. The process of claim 5 wherein said complexing agent is substituted with alkyl, aryl, or organic alcohol groups.

7. The process of claim 5 wherein said complexing agent is N-methylacetamide, pyridine, substituted pyridines, diethylmethylamine, methyldiethanolamine or tetramethylurea.

8. The process of claim 5 wherein the ratio of said complexing agent to said anthraquinone in said polar organic solvent is about 1:32 to about 1:1.

9. The process of claim 8 wherein the ratio of said complexing agent to said anthraquinone in said polar organic solvent is about 1:16 to about 1:3.

10. The process of claim 9 wherein the ratio of said complexing agent to said anthraquinone in said polar organic solvent is about 1:8.

11. The process of claim 1 wherein said polar organic solvent is selected from N,N-dimethylacetamide, N-methyl-2-pyrrolidinone, N,N-dimethylformamide and mixtures thereof.

12. The process of claim 1 wherein said feed gas also contains nitrogen, methane, other low molecular weight hydrocarbon gases, or mixtures thereof.

13. The process of claim 1 wherein said feed gas also contains COS, $CS_2$, or mercaptans which are converted to hydrogen sulfide by reaction with said anthrahyroquinone.

14. The process of claim 4 wherein the $pK_b$ value of said complexing agent is less than about 13.0.

15. The process of claim 14 wherein the $pK_b$ value of said complexing agent is less than about 9.0.

16. The process of claim 15 wherein the $pK_b$ value of said complexing agent is less than about 6.0.

17. A process for converting hydrogen sulfide to sulfur and hydrogen comprising:
providing a polar organic solvent having an anthraquinone and water dissolved therein, said water being dissolved in said solvent in an amount of from about 0.5 to about 5.0 moles of said water to moles of said anthraquinone;
contacting a feed gas containing hydrogen sulfide with said polar organic solvent;
reacting said hydrogen sulfide gas with said anthraquinone to produce sulfur and an anthrahydroquinone in said solvent, said water increasing the amount of said sulfur which is precipitated and recovered from said solvent; and
dehydrogenating said anthrahydroquinone to anthraquinone and hydrogen, said water increasing the selectivity of anthrahydroquinone conversion to anthraquinone and hydrogen.

18. The process of claim 17 wherein said amount of water which is added to said solvent is from about 0.75 to about 2.0 moles of said water to moles of said anthraquinone.

19. The process of claim 18 wherein said amount of water which is added to said solvent is from about 1.0 to about 1.5 moles of said water to moles of said anthraquinone.

20. The process of claim 17 wherein said solvent has a complexing agent dissolved therein, said complexing agent reacting with said hydrogen sulfide to form an ion complex.

21. The process of claim 20 wherein said complexing agent is amines, amides, ureas, nitrogen containing heterocyclic aromatics, quanidines, imidazoles, or mixtures thereof.

22. The process of claim 21 wherein said complexing agent is substituted with alkyl, aryl, or organic alcohol groups.

23. The process of claim 21 wherein said complexing agent is N-methylacetamide, pyridine, substituted pyridines, diethylmethylamine, methyldiethanolamine or tetramethylurea.

24. The process of claim 20 wherein the ratio of said complexing agent to said anthraquinone is about 1:32 to about 1:1.

25. The process of claim 24 wherein the ratio of said complexing agent to said anthraquinone is about 1:16 to about 1:2.

26. The process of claim 25 wherein the ratio of said complexing agent to said anthraquinone is about 1:5.

27. The process of claim 17 wherein said dehydrogenation reaction is carded out at a temperature of about 150° C. to about 350° C.

28. The process of claim 20 wherein the $pK_b$ value of said complexing agent is less than about 13.0.

29. The process of claim 28 wherein the $pK_b$ value of said complexing agent is less than about 9.0.

30. The process of claim 29 wherein the $pK_b$ value of said complexing agent is less than about 6.0.

31. The process of claim 17 wherein said anthraquinone, said water, said complexing and said solvent are recycled from said dehydrogenating step to said contacting step.

* * * * *

UNITED STATES PATENT AND TRADEMARK OFFICE
CERTIFICATE OF CORRECTION

PATENT NO. : 5,334,363
DATED : August 2, 1994
INVENTOR(S) : Mark A. Plummer

It is certified that error appears in the above-indentified patent and that said Letters Patent is hereby corrected as shown below:

Col. 6, Line 48:   Delete "50" and Insert --5.0--.

Signed and Sealed this

Tenth Day of June, 1997

Attest:

BRUCE LEHMAN

Attesting Officer     Commissioner of Patents and Trademarks